United States Patent

Barber et al.

[11] Patent Number: 5,641,965
[45] Date of Patent: Jun. 24, 1997

[54] IMAGE RECONSTRUCTION

[75] Inventors: David Charles Barber; Brian Hilton Brown, both of Sheffield, England

[73] Assignee: British Technology Group Limited, London, England

[21] Appl. No.: 428,214

[22] PCT Filed: Nov. 19, 1993

[86] PCT No.: PCT/GB93/02377

§ 371 Date: Jul. 14, 1995

§ 102(e) Date: Jul. 14, 1995

[87] PCT Pub. No.: WO94/12947

PCT Pub. Date: Jun. 9, 1994

[30] Foreign Application Priority Data

Nov. 20, 1992 [GB] United Kingdom ............ 9224403
Nov. 26, 1992 [GB] United Kingdom ............ 9224805

[51] Int. Cl.[6] .................................................. A61B 6/03
[52] U.S. Cl. ................... 250/363.04; 250/363.03; 378/901
[58] Field of Search .............. 378/4, 901; 364/413.19, 364/413.2, 413.21; 250/363.02, 363.03, 363.04

[56] References Cited

U.S. PATENT DOCUMENTS 5,079,697  1/1992  Chesler ............ 364/413.2
5,490,516  2/1996  Hutson ............ 128/696

OTHER PUBLICATIONS

Llacer & Meng: "Matrix–based image reconstruction methods for tomography", IEEE Transaction on Nuclear Science, vol. NS–32, No. 1, Feb. 1985, pp. 855–864.

*Primary Examiner*—David P. Porta
*Assistant Examiner*—David Vernon Bruce
*Attorney, Agent, or Firm*—Cushman, Darby & Cushman IP Group of Pillsbury Madison & Sutro LLP

[57] ABSTRACT

The invention provides a back-projection image reconstruction method or algorithm of the type $B(FB)^{-1}g=c$, where c is the image data vector which is to be reconstructed, g is, arranged in suitable form, the measurement data vector from which the image data vector c is to be reconstructed, F is a matrix representing the forward operation from c to g and B is a matrix representing the corresponding direct back-projection operation, characterised in that for the matrix $(FB)^{-1}$ there is substituted the equivalent, computationally more amenable, matrix product $WQ^{-1}W^*$, wherein $W^*$ is the complex conjugate of W, $Q^{-1}$ is the inverse of a matrix Q obtainable from the matrix FB by the operation $Q=W^*(FB)W$ and W is a matrix related to the Fourier Transform and defined in the specification.

6 Claims, No Drawings

IMAGE RECONSTRUCTION

This invention relates to the reconstruction of images, particularly tomographic images representing the distribution of some characteristic across a sectional plane of a body under investigation, from measurements made peripherally of the sectional plane.

The invention relates particularly, but not exclusively, to the SPECT (single photon emission computed tomography) and PET (positron emission tomography) tomographic techniques and to that known variously as electrical impedance tomography or applied potential tomography and referred to hereinafter as EIT, in which electrical signals applied peripherally to points of a body under investigation result, at other peripheral points, in electrical voltages or currents of which the values are measured and processed to form an image representing the distribution of electrical conductivity or resistivity over a section of the body. Such techniques have been described in, for example, a paper entitled "Applied potential tomography" by D. C. Barber and B. H. Brown published in J.Phys. E: Sci.Instrum., Vol. 17 (1984), pages 723–33, and in other papers referred to therein or published subsequently.

EIT has a promising future in clinical investigation of the human body, because it is a relatively inexpensive tomographic technique in terms of the equipment required, is essentially non-invasive, enables data to be rapidly collected and processed, and can be used for continuous monitoring.

In clinical use of the EIT technique, typically, a ring of spaced electrodes, say 16 in number, are positioned round and in contact with a body segment such as the thorax and an alternating current driving signal of a few milliamps at a frequency of, say, 50 kHz is applied between two of the electrodes while the resulting currents or voltages between remaining pairs of electrodes are measured and their values stored for processing. The driving signal is applied successively to different pairs of electrodes, and at each step the signals at the remaining pairs of electrodes are measured and their values stored, so as to maximise the amount of independent data which is obtained and which is then processed to obtain maximum resolution of the reconstructed image. The number of electrodes employed imposes an upper limit on the amount of independent data which can be obtained, and to increase the amount of data available, and thus the image resolution obtainable, it is necessary to increase the number of electrodes employed. There remains, however, a further problem: reconstruction of an image from the measured data is essentially a problem of matrix algebra, and, as the amount of data to be processed increases, the difficulty involved in applying the currently-employed reconstruction algorithms increases disproportionately. This problem is encountered not only in connection with EIT but also with other computed tomographic techniques, such as SPECT and PET, which employ back-projection from measured data to derive a reconstructed image.

Accordingly, it is an object of the present invention to provide an improved reconstruction method or algorithm for deriving a reconstructed tomographic image from the relevant basic measured data, and an improved method of formulating a critical part of such algorithm.

According to the invention there is provided a back-projection image reconstruction method or algorithm of the type $B(FB)^{-1}g=c$, where c is the image data vector which is to be reconstructed, g is, arranged in suitable form, the measurement data vector from which the image data vector c is to be reconstructed, F is a matrix representing the forward operation from c to g and B is a matrix representing the corresponding direct back-projection operation, characterised in that for the matrix $(FB)^{-1}$ there is substituted the equivalent, computationally more amenable, matrix product $WQ^{-1}W^*$ wherein $W^*$ is the complex conjugate of W, $Q^{-1}$ is the inverse of a matrix Q obtainable from the matrix FB by the operation $Q=W^*(FB)W$ and W is a matrix related to the Fourier Transform and defined as $$W = \begin{vmatrix} W_0 & W_0 & W_0 & W_0 & \ldots & W_0 \\ W_0 & W_1 & W_2 & W_3 & \ldots & W_{(N-1)} \\ W_0 & W_2 & W_4 & W_6 & \ldots & W_{2(N-1)} \\ . & & & & & \\ . & & & & & \\ . & & & & & \\ W_0 & W_{(N-1)} & & & \ldots & W_{(N-1)(N-1)} \end{vmatrix},$$

each of the elements $W_n$ of W being an N×N diagonal matrix $$W_n = N^{-1/2} \begin{vmatrix} w^n & & & \\ & w^n & & 0 \\ & & . & \\ & 0 & & . \\ & & & w^n \end{vmatrix}$$

in which $w^n = \exp(-2j\pi n/N)$ and N is a multiple integral power of an integer and is equal to the number of data profiles collected and assembled to form the measurement data vector g.

According to the invention as seen from a slightly different point of view there is provided a method of formulating the matrix $(FB)^{-1}$, for use in carrying out a back-projection image reconstruction method or algorithm of the type $B(FB)^{-g}=c$, where c is the image data vector which is to be reconstructed, g is, arranged in suitable form, the measured data vector from which the image data vector c is to be reconstructed, F is a matrix representing the forward operation from c to g and B is a matrix representing the corresponding direct back-projection operation, characterised in that in substitution for the matrix $(FB)^{-1}$ there is formulated the equivalent, computationally more amenable, matrix product $WQ^{-1}W^*$, wherein i* is the complex conjugate of W, $Q^{-1}$ is the inverse of a matrix Q obtainable from the matrix FB by the operation $Q=W^*(FB)W$ and W is a matrix related to the Fourier Transform and defined as $$W = \begin{vmatrix} W_0 & W_0 & W_0 & W_0 & \ldots & W_0 \\ W_0 & W_1 & W_2 & W_3 & \ldots & W_{(N-1)} \\ W_0 & W_2 & W_4 & W_6 & \ldots & W_{2(N-1)} \\ . & & & & & \\ . & & & & & \\ . & & & & & \\ W_0 & W_{(N-1)} & & & \ldots & W_{(N-1)(N-1)} \end{vmatrix},$$

each of the elements $W_n$ of W being an N×N diagonal matrix $$W_n = N^{-1/2} \begin{vmatrix} w^n & & & \\ & w^n & & 0 \\ & & \cdot & \\ & 0 & & \cdot \\ & & & & w^n \end{vmatrix}$$

in which $w^n = \exp(-2j\pi n/N)$ and N is a multiple integral power of an integer and is equal to the number of data profiles collected and assembled to form the measurement data vector g.

The improved reconstruction process or algorithm according to the invention is not limited in its application to the electrical impedance or applied potential tomographic technique referred to above. It is a general method which can be applied to all computed tomographic techniques: for example, it can be applied to radioisotope tomography. However, it will be disclosed and described below principally in its application to EIT.

In a known application of EIT, as referred to above, 16 electrodes are placed in a ring round a body to be examined and a driving current is applied in turn to each of the 16 mutually adjacent pairs of electrodes while, at each step, the resulting received signal at each of the 16 pairs is measured and recorded. If the successive electrode pairs round the ring are labelled 1,2, ... 16, the data element representing the signal received at pair m while the driving signal is applied to pair k may be labelled (k,m). For each drive, for example driving at electrode pair 1, signals can be received at 16 electrode pairs; so all the received data may be written in a 16×16 array, thus:

```
1,1   1,2   1,3 ..... 1,16
2,1   2,2 ......... 2,16
 .
 .
 .
16,1 ............ 16,16.
```

It will be observed that in this form the data values which represent driving and receiving at the same electrode pair lie on the principal diagonal of the array.

For a reason which will become apparent, however, it will be preferred for the purposes of the invention to modify this array by cycling all the elements of the ith row (i−1) places to the left so that the element (i,i) which was originally on the diagonal of the array becomes the element at the left-hand end of the row and elements which were to the left of it are cycled round to the right-hand end of the row. This re-arranged array may be described as being "left-justified".

The rows of the left-justified array may then be strung together, one after another, to provide a data vector g, i.e. (1,1 1,2 ... 1,6 2,2 2,3 ... 2,16 2,1 ... 16,16 16,1 ... 16,15).

The elements of g are not all independent of one another, since (k,m)=(m,k) and (k,k) can be derived from the rest of the data in the same row of the data array. In fact, for a 16-electrode system there are 256 possible measurements but only 120 are independent.

Now the values of the measured data represented by the elements of data vector g are functions of the resistivity distribution of the body section under investigation, and the object of the investigation is to derive from the vector g of measured data a vector c of image data defining an image which will represent the resistivity distribution. The measured data of vector g are related to the body section (as represented by the image vector c) by the relationship $$g = Fc$$

where F is a matrix representing the "forward" operation from c to g. A favoured way of recovering the elements of the image vector c from the vector g of measured data is the method known as back projection, and if the back projection operation is represented by a matrix B it may be shown that $$B(FB)^{-1}g = c$$

In this operation, $(FB)^{-1}$ is a matrix which converts the data vector g into a data vector g' which, when back projected, gives the image data vector c. In order to carry out this operation it is necessary to calculate the matrix $(FB)^{-1}$. Calculation of the matrix FB is fairly easy, but inverting it can be a difficult problem, since its dimensions may be large. As noted above, a 16-electrode system can produce 256 possible measurements, of which 120 are independent, and this means that the matrix FB is 120×120 in size; but if the number of electrodes is increased to 32, the size of the matrix FB increases to 496×496, and for a 64-electrode interleaved system which is also a possibility, the size of the matrix FB is 1024×1024. In either of these latter two cases, the matrix FB is of such size that it would be difficult to invert directly. However, the present invention provides a solution of the difficulty, as will be explained in what follows.

The back projection method represented by $$B(FB)^{-1}g = c$$

requires the operation $$(FB)^{-1}g = g'$$

as a first step: that, indeed, is why the matrix $(FB)^{-1}$ is required. In this, g' is a modified data vector from which the required image data vector c can be obtained directly by back projection as represented by $$Bg' = c$$

Now the operation $$(FB)^{-1}g = g'$$

implies, notionally, the inverse operation $$(FB)g' = g$$

and it is instructive to consider the nature of that notional operation. This may be illustrated by reference to the 16-electrode case, for which (ignoring the fact that the 256 data measurements are not all independent) the data vector g is a string of 256 data elements obtained by stringing together the rows of a 16×16 left-justified array and FB is a matrix of size 256×256. In the notional operation $$(FB)g' = g$$

the first element of g, i.e. (1,1), is obtained by multiplying g' by the first row of FB. Similarly, the seventeenth element of g, namely (2,2), is obtained by multiplying g' by row 17 of FB. However, if the electrodes were rotated one place to the right, (2,2) would become (1,1) without altering the facts of the reconstruction, and it therefore follows that row 17 of FB must be the same as row 1 of FB, but rotated or cycled 16 places to the right. Applying the same reasoning to other elements of g, it is seen that rows 17 to 32 of FB are obtained by taking rows 1 to 16 and rotating or cycling them 16 places to the right, rows 33 to 48 are obtained by cycling rows 1 to 16 to the right by 32 places, and so on. Clearly, then, FB has a highly regular structure, a fact which may be turned to advantage in finding its inverse $(FB)^{-1}$: FB is 256×256 in size, and has the form:

$$\begin{vmatrix} A_1 & A_2 & A_3 & & A_N \\ A_N & A_1 & A_2 & & A_{N-1} \\ A_{N-1} & A_N & A_1 & & A_{N-2} \\ \cdot \\ \cdot \\ \cdot \\ A_2 & A_3 & A_4 & \ldots A_N & A_1 \end{vmatrix}$$

where the $A_i$ are sub-matrices of size 16×16 and N=16.

As is well known, a square matrix A (such as FB) can in principle be inverted by first decomposing it into three matrices, thus:

$$A = U^T R V$$

where U and V are orthonormal matrices which are easy to invert (their inverses are their transposes) and R is a diagonal matrix, with non-zero elements only on its principal diagonal, which is also easy to invert. If A can be decomposed in this way its inverse $A^{-1}$ is then easily obtained as $$A^{-1} = V^T R^{-1} U$$

However, U, V and R have to be computed, and in practice this would usually be an impractically lengthy computation and subject to unacceptably large numerical computation rounding errors. This known "single value decomposition" method therefore does not provide a practical solution to the problem of inverting the matrix FB.

In accordance with the invention however, inversion of the matrix FB can be achieved, in effect, by making use of a matrix W which is related to the Fourier Transform and may be constructed as follows:

First, let $$w = \exp(-2j\pi/N)$$

where exp is the exponential function, $J=(-1)^{1/2}$ and N is the number of mutually adjacent pairs of electrodes to which a driving signal is applied in obtaining the data vector g. (It may be noted that because of the relationship of the matrix W to the Fourier Transform it is a requirement that N shall be a multiple integral power of an integer; thus $N=16=2^4$ for the example discussed above). Then it is a property of the exponential function that $$w^n = \exp(-2j\pi n/N)$$

If n is allowed to assume the value of each integer from zero to (N−1) and also the value of each product of two such integers, and for each such value of n there is formed an N×N diagonal matrix $W_n$ defined as $$W_n = N^{-1/2} \begin{vmatrix} w^n & & & \\ & w^n & 0 & \\ & 0 & \cdot & \\ & & & w^n \end{vmatrix},$$

then these matrices $W_n$ can be arranged as the elements of the required matrix W, with $$W = \begin{vmatrix} W_0 & W_0 & W_0 & W_0 & \ldots & W_0 \\ W_0 & W_1 & W_2 & W_3 & \ldots & W_{(N-1)} \\ W_0 & W_2 & W_4 & W_6 & \ldots & W_{2(N-1)} \\ \cdot \\ \cdot \\ \cdot \\ W_0 & W_{(N-1)} & & & \ldots & W_{(N-1)(N-1)} \end{vmatrix}.$$

It can be shown that if FB is subjected to the operation $$Q = W^*(FB)W$$

where $W^*$ is the complex conjugate of W, then Q has the form $$Q = \begin{vmatrix} Q_1 & & & \\ & Q_2 & 0 & \\ & & \cdot & \\ & 0 & & \cdot \\ & & & Q_{16} \end{vmatrix}$$

where the $Q_i (i=1, \ldots 16)$ are 16×16 matrices. Because none of the rows or columns of any of these component matrices overlaps those of any other, the inverse of Q is given by $$Q^{-1} = \begin{vmatrix} Q_1^{-1} & & & \\ & Q_2^{-1} & 0 & \\ & & \cdot & \\ & 0 & & \cdot \\ & & & Q_{16}^{-1} \end{vmatrix}.$$

Since each of the matrices $Q_i$ is only 16×16, it can easily be inverted; and thus the inverse of Q can also be easily obtained. The situation is, in fact, rather more complicated than is suggested above, because although Q is 256×256 its rank is only 120×120. However, there are well established methods for dealing with this complication, which therefore does not represent a problem.

This derivation from FB of the matrix Q and its inverse $Q^{-1}$ affords a relatively easy way of inverting FB, even when FB is of large size. Writing FB as $$FB = WQW^*$$

it follows that its inverse may be written as $$(FB)^{-1} = WQ^{-1}W^*$$

Thus, for the back projection of the data vector g to yield the image vector c, the invention provides the process or algorithm $c = Bg' = B(FB)^{-1}g = BWQ^{-1}W^*g$ i.e. $c = BWQ^{-1}W^*g$.

Benefits of decomposing $(FB)^{-1}$ in this way can be illustrated even in the 16-electrode case. If $(FB)^{-1}$ is not decomposed in this way, the computation of g' from g requires (for 16 electrodes) 256×256 operations (i.e. over 65000 operations). If $(FB)^{-1}$ is first decomposed as above, then computation of g' involves, first, computation of $W^*g$ (which is fast, because it can use the Fast Fourier Transform (FFT)), then multiplication by $Q^{-1}$ (which represents at most 16×16×16 operations, and is thus 16 times faster than direct multiplication by $(FB)^{-1}$, and then multiplication by W (which again is fast because it can use the FFT). Overall an approximately 3-fold increase in speed may be expected for the 16 electrode case, a 5-fold increase for the case of 32 electrodes and the correspondingly greater number of data elements in the data vector g in that case, and still greater increases in speed for larger numbers. These increases in the speed of processing are, of course, advantages which are additional to the fact that without the described decomposition of FB it might be very difficult or impossible, if FB is of large size, to obtain its inverse $(FB)^{-1}$. Direct inversion of a 1024×1024 matrix, for example, is not an enterprise to be undertaken lightly; but using the present invention this task reduces to inverting 32 matrices, each of size 32×32, which is much easier.

Although the invention has been illustrated, above, by a description of its application in connection with electrical impedance or applied potential tomography, it is to be understood that it may be utilised in back-projection methods of image reconstruction in any of the various tomographic techniques, including x-ray computed tomography, magnetic resonance imaging, and radioisotope tomography (single photon emission computed tomography, or SPECT, and positron emission tomography, PET). All of these involve formulating a respective $(FB)^{-1}$ function, and in all of them this task, and the image reconstruction of which it is a part, can, with advantage, be accomplished by the method of the invention.

Refering to SPECT and PET in particular, one factor which has to be taken into account is the gamma-ray attenuation which occurs in the tissue of the body section under investigation before the remaining unabsorbed gamma radiation is detected by the gamma camera. For SPECT, there does exist a theoretical method for correcting the consequential distortion of the collected data, but it is very unstable and is therefore not used in practice. An alternative method of correction for attenuation in SPECT uses an iterative approach, but this has convergence problems and in any case is time consuming. There are also one or two ad hoc methods which give approximate solutions: the correction they provide is incomplete and the images they produce are therefore still incorrect, but they are fast and are the methods which are used for SPECT in practice. Only the iterative technique is able to take full account of the fact that gamma ray attenuation is not uniform throughout the body under investigation, but a CT image is needed for this and it is therefore rarely done. The method according to the invention corrects for gamma ray attenuation in SPECT better than the above-mentioned ad hoc methods and is not much slower, and is faster than the iterative technique. It may therefore be expected to become widely seen as an improvement in connection with SPECT, as well as in EIT. As for PET, complete correction for attenuation can be achieved in theory, but in practice there are operational problems which make it much more cost-effective to use a SPECT-like approach. This is increasingly being done, using the above-mentioned ad hoc techniques; and again, in PET as in SPECT, it may be expected that the invention will provide an important improvement.

In applying the invention to any of the techniques mentioned above, it is necessary to formulate the matrix (FB), and its components F and B, in a manner which suitably embodies the physics of the situation. In connection with x-ray computed tomography, for example, where the linear attenuation co-efficient of the x-rays is the essential nature of the process, and where x-ray scattering is insignificant and can be ignored, and distance-dependent point spread function (PSF) does not come into consideration, the forward transformation matrix F can be a relatively simple formulation $F_o$ containing no error-correction terms for either scattering or PSF. As a practical matter, $F_o{}^t$, the transpose of $F_o$, can be employed as the formulation of B, and the matrix (FB) is thus formulated relatively simply as $(F_o F_o{}^t)$. In applying the invention to SPECT, in which suitable account must be taken of attenuation of the emitted radiation, this may advantageously be done by incorporating the necessary corrections into the F matrix so as to obtain an attenuation-cognisant forward transformation matrix $F_a$; and in this case also, though $F_a$ is somewhat more complicated than $F_o$ referred to above, it is appropriate to use $F_a{}^t$, the transpose of $F_a$, as the formulation of B and thus to use $(F_a F_a{}^t)$ as the formulation of the matrix (FB). In applying the invention to SPECT and PET, the forward transformation matrix F can also advantageously take account not only of attenuation but also of PSF. In this case, an appropriately more complicated matrix $F_g$, taking proper account of all these factors and the geometry of the situation, may be formulated as the matrix F. In principle, it would be appropriate also to use $F_g{}^t$, the transpose of $F_g$, as the matrix B in computing (FB). However, in view of the increased complexity of $F_g$, as compared with $F_a$, the computation of $F_g{}^t$ would be considerably slower than computation of $F_a{}^t$, and it is preferred (and found allowable in practice) in this case to use $(F_g F_a{}^t)$ as the matrix (FB).

In the definition of w and the matrix W in the foregoing disclosure of the invention as applied to EIT, N was defined as being equal to the number of mutually adjacent pairs of electrodes to which a driving signal is applied in obtaining the data vector g. More generally, and particularly as regards application of the invention to SPECT or PET, N may be defined as being equal to the number of data profiles collected and assembled to form the measurement data vector g. Although N will often be a multiple power of 2, e.g. 16, 32 or 64, it may be a power of some other integer. For example, 64 profiles are often collected in practising SPECT, but 81 ($=3^4$) has some theoretical advantages and may also prove advantageous in practice.

We claim:

1. A back-projection image reconstruction method of the type $B(FB)^{-1}g = c$, where c is the image data vector which is to be reconstructed, g is, arranged in suitable form, the measurement data vector from which the image data vector c is to be reconstructed, F is a matrix representing the forward operation from c to g and B is a matrix representing the corresponding direct back-projection operation, wherein for the matrix $(FB)^{-1}$ there is substituted the equivalent, computationally more amenable, matrix product $WQ^{-1}W^*$, wherein $W^*$ is the complex conjugate of W, $Q^{-1}$ is the inverse of a matrix Q obtainable from the matrix FB by the operation $Q = W^*(FB)W$ and W is a matrix related to the Fourier Transform and defined as $$W = \begin{vmatrix} W_0 & W_0 & W_0 & W_0 & \ldots & W_0 \\ W_0 & W_1 & W_2 & W_3 & \ldots & W_{(N-1)} \\ W_0 & W_2 & W_4 & W_6 & \ldots & W_{2(N-1)} \\ \cdot & & & & & \\ \cdot & & & & & \\ \cdot & & & & & \\ W_0 & W_{(N-1)} & & & \ldots & W_{(N-1)(N-1)} \end{vmatrix},$$

each of the elements $W_n$ of W being an N×N diagonal matrix $$W_n = N^{-1/2} \begin{vmatrix} w^n & & & \\ & w^n & & 0 \\ & & \cdot & \\ & 0 & & \cdot \\ & & & & w^n \end{vmatrix}$$

in which $w^n = \exp(-2j\pi n/N)$ and N is a multiple integral power of an integer and is equal to the number of data profiles collected and assembled to form the measurement data vector g.

2. A method of formulating the matrix $(FB)^{-1}$, for use in carrying out a back-projection image reconstruction method of the type $B(FB)^{-1}g = c$, where c is the image data vector which is to be reconstructed, g is, arranged in suitable form, the measured data vector from which the image data vector c is to be reconstructed, F is a matrix representing the forward operation from c to g and B is a matrix representing the corresponding direct back-projection operation, wherein in substitution for the matrix $(FB)^{-1}$ there is formulated the equivalent, computationally more amenable, matrix product $WQ^{-1}W^*$ wherein $W^*$ is the complex conjugate of W, $Q^{-1}$ is the inverse of a matrix Q obtainable from the matrix FB by the operation $Q = W^*(FB)W$ and W is a matrix related to the Fourier Transform and defined as $$W = \begin{vmatrix} W_0 & W_0 & W_0 & W_0 & \ldots & W_0 \\ W_0 & W_1 & W_2 & W_3 & \ldots & W_{(N-1)} \\ W_0 & W_2 & W_4 & W_6 & \ldots & W_{2(N-1)} \\ \cdot & & & & & \\ \cdot & & & & & \\ \cdot & & & & & \\ W_0 & W_{(N-1)} & & & \ldots & W_{(N-1)(N-1)} \end{vmatrix},$$

each of the elements $W_n$ of W being an N×N diagonal matrix $$W_n = N^{-1/2} \begin{vmatrix} w^n & & & \\ & w^n & & 0 \\ & & \cdot & \\ & 0 & & \cdot \\ & & & & w^n \end{vmatrix}$$

in which $w^n = \exp(-2j\pi n/N)$ and N is a multiple integral power of an integer and is equal to the number of data profiles collected and assembled to form the measurement data vector g.

3. A method as claimed in claim 1 or claim 2, wherein the matrix (FB) from which the matrix Q is derived is formulated as $(FF^t)$, where $F^t$ is the transpose of F.

4. A method as claimed in claim 3, wherein the matrix F is formulated as a matrix $F_o$ incorporating no error corrections for attenuation, scatter or point spread function, and the matrix (FB) is formulated as $(F_o F_o^t)$.

5. A method as claimed in claim 3, wherein the matrix F is formulated as a matrix $F_a$ incorporating error corrections for attenuation and the matrix (FB) is formulated as $(F_a F_a^t)$.

6. A method as claimed in claim 1 or claim 2, wherein the matrix (FB) from which the matrix Q is derived is formulated as $(F_g F_a^t)$, in which $F_g$ is a formulation of F which incorporates error corrections for attentuation, scatter and point spread function and $F_a^t$ is the transpose of a formulation $F_a$ of F which incorporates error corrections for attenuation but not for point spread function.

* * * * *